United States Patent [19]
Fuisz

[11] Patent Number: 5,733,269
[45] Date of Patent: Mar. 31, 1998

[54] METHOD AND KIT FOR POSITIONING TRANSDERMAL DELIVERY SYSTEM

[75] Inventor: Richard C. Fuisz, Great Falls, Va.

[73] Assignee: Fuisz Technologies Ltd., Chantilly, Va.

[21] Appl. No.: 616,173

[22] Filed: Mar. 15, 1996

[51] Int. Cl.⁶ .................................................. A61M 35/00
[52] U.S. Cl. ........................................ 604/290; 604/116
[58] Field of Search ....................... 604/115, 116, 604/289, 290, 304, 306; 206/440, 828; 424/447, 449

[56] References Cited

U.S. PATENT DOCUMENTS

| | | | |
|---|---|---|---|
| 4,610,806 | 9/1986 | Rosen . | |
| 4,838,854 | 6/1989 | Kuzmanovich | 604/116 |
| 5,009,644 | 4/1991 | McDonald | 604/116 |
| 5,120,546 | 6/1992 | Hansen, et al. . | |
| 5,147,307 | 9/1992 | Gluck | 604/116 |
| 5,176,917 | 1/1993 | Müller . | |
| 5,224,928 | 7/1993 | Sibalis, et al. . | |
| 5,286,254 | 2/1994 | Shapland, et al . | |
| 5,462,743 | 10/1995 | Turner, et al. . | |
| 5,482,965 | 1/1996 | Rajadhyaksha . | |
| 5,490,415 | 2/1996 | Mak, et al. . | |
| 5,569,237 | 10/1996 | Beckenstein | 604/116 |
| 5,606,165 | 2/1997 | Sessions et al. | 128/888 |

*Primary Examiner*—Robert A. Clarke
*Assistant Examiner*—David J. Cho
*Attorney, Agent, or Firm*—Sandra M. Nolan; Richard D. Schmidt

[57] ABSTRACT

A method and kit for positioning a transdermal drug delivery system useful in treating individuals having maladies requiring topical, subcutaneous, intra-lesional and systemic administration of one or more drugs for a prolonged period of time is disclosed. A method for employing the present invention kit allows a patient to accurately self-administer a prolonged treatment regimen including a transdermal delivery system without the substantial involvement of medical personnel.

20 Claims, 3 Drawing Sheets

```
STEP 10-SELECTING THE TREATMENT AREA ON THE PATIENT
                            ↓
STEP 20-MARKING THE TREATMENT AREA
                            ↓
STEP 30-SELECTING A TRANSDERMAL DELIVERY SYSTEM
HAVING A PATTERN ASSOCIATED THEREWITH
COMPLEMENTARY TO THE MARK PLACED IN STEP 20
                            ↓
STEP 40-ALIGNING THE COMPLEMENTARY MARK ASSOCIATED
WITH THE TRANSDERMAL DELIVERY SYSTEM WITH THE
MARK ON THE TREATMENT AREA
                            ↓
STEP 50-REMOVABLY ATTACHING THE TRANSDERMAL
DELIVERY SYSTEM TO THE TREATMENT AREA
                            ↓
STEP 60-REPEATING STEP 30 THROUGH STEP 50 TO
REPLACE THE TRANSDERMAL DELIVERY SYSTEM
```

5,733,269

METHOD AND KIT FOR POSITIONING TRANSDERMAL DELIVERY SYSTEM

TECHNICAL FIELD

The present invention relates to drug delivery systems, and more specifically, to a method and kit for positioning transdermal and topical drug delivery systems.

BACKGROUND OF THE INVENTION

For several years, transdermal drug delivery systems have been employed to effectively introduce certain drugs into the bloodstream through unbroken skin. Aside from comfort and convenience, transdermal systems avoid the gastrointestinal tract, the delivery rate control problems and potential toxicity concerns associated with traditional administration techniques, such as oral, intramuscular or intravenous delivery. For example, such systems have proven particularly effective in the delivery of melatonin and other natural hormones to the body, since transdermal delivery mimics the body's own system of secretion. Transdermal devices known in the art include reservoir type devices including membranes, pressure-sensitive adhesive matrices and skin patches. An example of a new type of transdermal drug delivery, one in which one or more drugs is delivered topically and/or subdermally, without passing into the bloodstream, is described in co-pending U.S. application Ser. No. 08/613,710 filed on Mar. 11, 1996 to Fuisz.

The use of transdermal delivery systems provides the advantages of (1) reducing the need for intensive physician or other medical personnel involvement in a particular treatment, thus significantly reducing the burden and costs of repeated visits to a health care professional, and (2) improving the overall efficacy of a treatment due to the removal of a patient's need to adhere to the rigorous and lengthy administration schedule of topical and/or subcutaneous drug delivery.

A necessary factor in the effective use of transdermal and topical delivery systems is the proper placement of the delivery system. Proper placement in this context not only includes exact physical location of the delivery system, but also often includes the concept of consistent proper placement of the delivery system over the course of a treatment regimen. For example, where a transdermal delivery system is used to treat a skin cancer, as more fully described in co-pending U.S. application Ser. No. 08/613,710 filed Mar. 11, 1996, it is critical for successful treatment that the drug(s) delivered are consistently delivered to the exact location of the lesion on the patient. Where the lesion is visually difficult to locate, or the lesion disappears or is visually reduced during treatment, traditional transdermal delivery systems, where a patient applies and removes the system numerous times during the treatment period, are ineffective.

Traditionally, positioning and placement of a transdermal delivery system has been left to the patient, often requiring the assistance of a medical professional. Additionally, the patient has not been provided with an acceptable method or system to aid in the proper positioning and placement of the transdermal delivery system. Accordingly, patients and health care professionals alike have had to rely upon repeated visual inspection and alignment of the transdermal delivery system with the appropriate area, a system and method inherently inaccurate at best. This is particularly true where the delivery system has been a relatively simple medicament bandage or similar system for puncture sites and the like.

Finally, most traditional uses of transdermal delivery systems have been utilized in connection with systemic delivery of one or more drugs, making the exact placement of the transdermal system on the patient of lesser importance.

Thus a need remains for a method and kit for positioning a drug delivery system capable of assisting a patient or health care professional in the repeated positioning and application of a topical delivery system for effective transdermal delivery of a drug or drugs.

SUMMARY OF THE INVENTION

The transdermal drug delivery system of the present invention overcomes the foregoing and other problems associated with traditional approaches by providing a quick, easy and accurate positioning and placement method and kit for use with a transdermal delivery system. As used herein, "transdermal delivery system" and "drug delivery system" shall mean delivery systems capable of transporting one or more drugs across the several layers of the skin, and either allowing passage of such drugs through to the bloodstream or simply providing local, subcutaneous and intra-lesional delivery without passage of the drugs to the bloodstream. Additionally, "transdermal delivery system" and "drug delivery system" shall include any and all systems used for positioning a drug delivery system, including, without limitation, medicament bandages and needle puncture sites.

Employing a prefered embodiment of the the positioning method and kit of the present invention, the appropriate area of the patient, for example a skin lesion, is located and marked using a pre-formed stamp including indelible ink. Preferably, the ink stamp marked comprises a horizontal line and a vertical line centered over the appropriate area. Since the ink is indelible, the target area need be located and marked only once during the treatment period. This is critical to the present invention since the proper treatement location is often more difficult to locate as treatment progresses. The transdermal delivery system, often is the form of a skin patch, also includes similar horizontal and vertical lines on its exposed bottom surface. By aligning the marks on the patch with the indelible ink stamp mark on the patient's skin, the patch is properly aligned upon each removal and reapplication of the patch.

Using the novel positioning system and kit of the present invention, the transdermal delivery system is easily and properly placed by the patient or other non-health care worker during treatment. The ease of use associated with the positioning method and system of the present invention allows patients or other non-health care personnel to provide effective prolonged treatment of certain maladies without the need for the numerous physician visits associated with traditional forms of treatment.

BRIEF DESCRIPTION OF THE DRAWINGS

For a more complete understanding of the present invention and the advantages thereof, reference is now made to the following description taken in conjunction with the accompanying drawings in which.

DETAILED DESCRIPTION OF THE DRAWINGS

The kit of the present invention includes at least one means for making a mark and at least one transdermal delivery system having a pattern associated with it that is complementary to the mark made by the marking means. The means for making the mark on the treatment area is used to semi-permanently mark the treatment area. Once marked, the complementary pattern associated with the transdermal delivery system is aligned with the mark on the treatment area to properly align and place the transdermal delivery system. Once aligned, the transdermal delivery system is removably attached to the treatment area. Since the treatment area is marked, subsequent transdermal delivery systems can be properly positioned and placed even where the treatment diminishes the ability to visually locate the treatment area.

The transdermal delivery system can be any type of transdermal delivery system, like a skin patch or multi-layered patch, and can be used alone or in conjunction with means for facilitating transdermal delivery of one or more drugs, like ionotophoresis. Preferably, the marking means is an ink stamp and utilizes indelible ink. Although ink is described herein, any suitable method for semi-permanently marking the treatment area can be used, if desired.

Figure 1A:
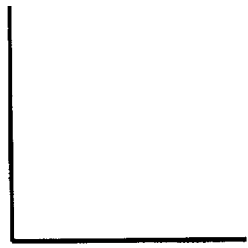
FIG. 1 is a top view of several of the types of ink stamps capable of use with the positioning method and kit of the present invention.
Figure 1B:
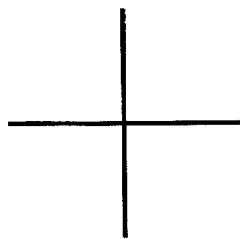
Figure 1C:
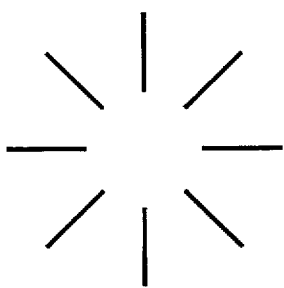

Referring to FIG. 1, there is shown types of marks used with the method and kit of the present invention. FIG. 1A illustrates perhaps the simplest, and therefore the preferred, mark consisting of a single horizontal line and a single vertical line, the intersection of the end points of these lines being centered over the area to be treated with a transdermal delivery system. FIG. 1B illustrates a variation of the mark illustrated in FIG. 1A and consists of a single horizontal line and a single vertical line forming a "cross-hair" pattern to be centered over the area to be treated with a transdermal delivery system. Finally, in FIG. 1C there is illustrated a radial pattern of multiple lines centered on the area to be treated. Although the foregoing marks are illustrated in the Drawings and discussed herein, it will be noted that any appropriate number of lines, including a single line, in any arrangement capable of assisting one in the positioning and placement of a transdermal delivery system, may be used, if desired.

Figure 4:
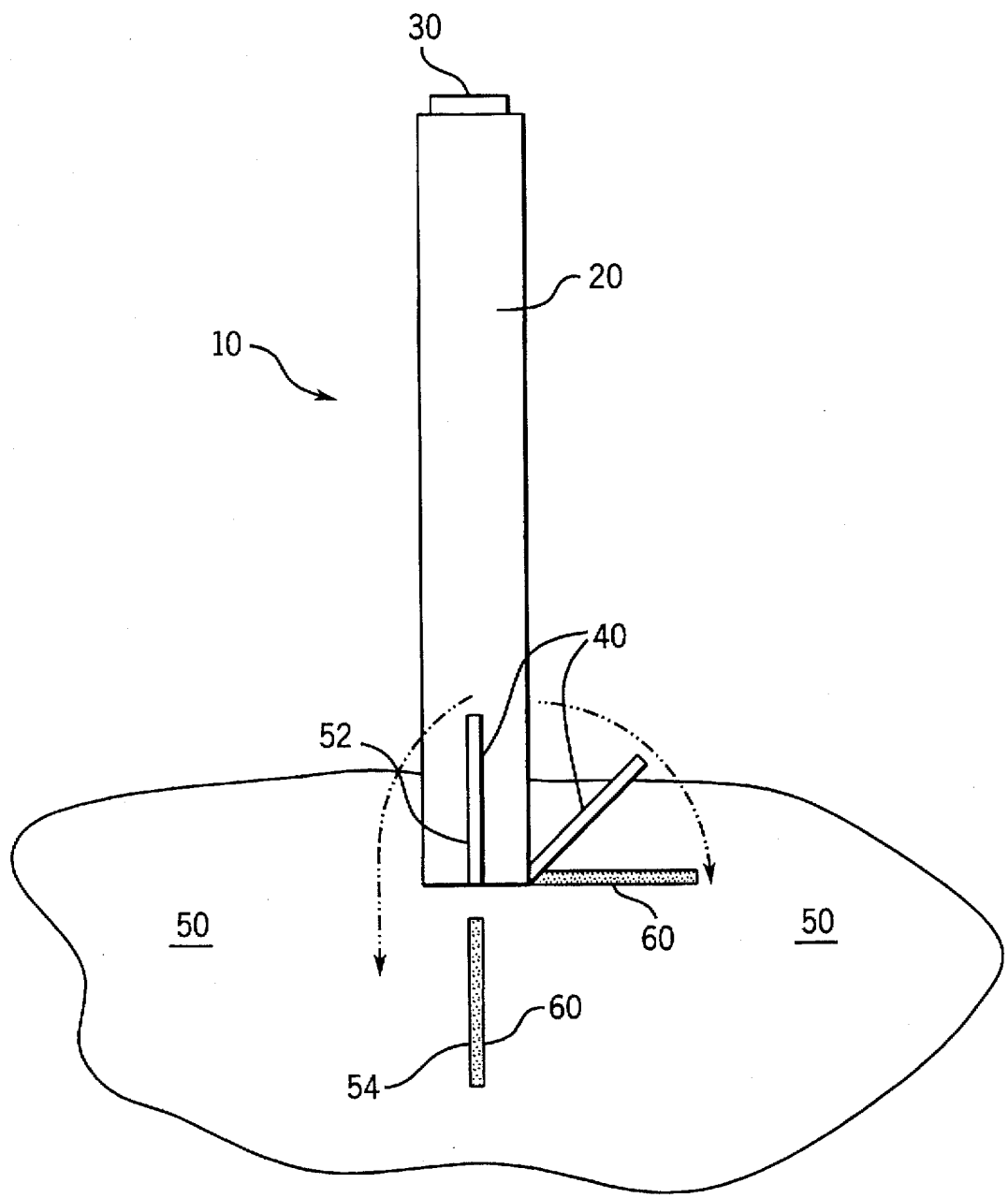
FIG. 4 is a side view of a marking device used in connection with the kit of the present invention.

Now referring to FIG. 4, there is shown one type of marking device used with the method and kit of the present invention. The marking device 10 includes a cylindrical body 20, a push button 30 located at the top of the body 20, and one or more marking wands 40 movably attached towards the bottom of the body 20. In use, the marking device 10 is placed adjacent to the treatment area 50 and the push button 30 is depressed, causing the one or more marking wands 40 to descend in an arc (dashed lines show path) from a first position 52 towards and in contact with a second position 54. The second position 54 is in contact with the treatment area 50. The marking wands 40 are preferably associated with a spring (not shown) such that the release of the push button 30 causes the springs to automatically return from the second position 54 to the first position 52.

As each of the marking wands 40 contact the treatment area 50 (i.e., the second position 54), a mark 60 is placed on the treatment area 50. When the push button 30 is released, the marking wands 40 reverse their path away from the second position 54 (i.e., treatment area 50) and return to the first position 52 (i.e., the body 20 of the marking device 10).

Preferably, the marking wands 40 rest within the cylindrical body 20 portion of the marking device when not in use. Although FIG. 4 depicts two marking wands 40 forming an "L" shape mark on the treatment area 50, it is noted that any number of marking wands 40, including a single marking wand, forming any suitable pattern, can be used, if desired.

To provide the mark 60 on the treatment area 50, the marking wands 40 preferably include means for delivering ink (not shown), preferably indelible ink. The means for delivering ink preferably is housed within the cylindrical body 20 of the marking device 10 and preferably feeds the ink to the marking wands 40 upon depression of the push button 30 or any other suitable means, or, alternatively, ink can be housed external to the marking device 10 and associated with the marking wands 40 by first causing the wands 40 to come into contact with the ink (e.g., ink pad) prior to placement adjacent to the treatment area 50. Although a manually-operated marking device 10 is depicted and described herein, it is noted that any suitable marking device capable of placing a mark on the treatment area can be used, if desired.

Figure 2A:
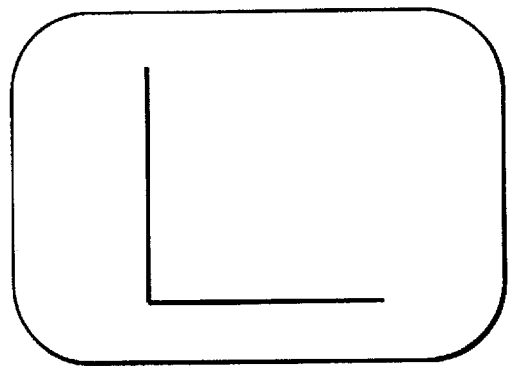
FIG. 2 is a bottom view of a transdermal drug delivery system including the positioning marks to be aligned with the indelible stamp.
Figure 2B:
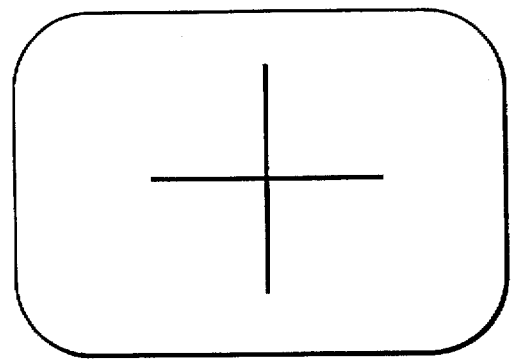
Figure 2C:
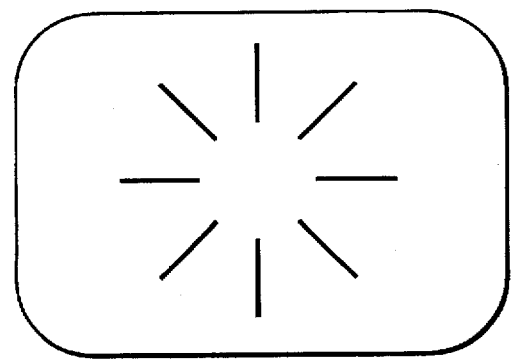

Referring now to FIG. 2, there is shown a bottom view of three transdermal delivery systems in a multi-layered patch form including the complementary pattern of the mark illustrated in FIGS. 1A–1C. FIG. 2A illustrates a multi-layered transdermal patch including the complementary pattern of mark illustrated in FIG. 1A. Likewise, illustrated in FIG. 2B is a multi-layered transdermal patch including the complementary pattern to the mark illustrated in FIG. 1B. Finally, illustrated in FIG. 2C is a multi-layered transdermal patch including the complementary pattern to the mark illustrated in FIG. 1C. Like the marks described above, the complementary pattern appearing on the bottom of the transdermal delivery system can be comprised of any number of lines or markings, including a single line or mark, in any suitable arrangement capable of assisting one in the positioning and placement of a transdermal delivery system. Additionally, the complementary patterns may appear on the transdermal delivery system in places other than the underneath bottom surface. For example, where a transparent or translucent patch design is employed, the marking may appear even on the top of the transdermal delivery system, since aligning the pattern with the mark will be facilitated by viewing the mark through the patch.

Figure 3:
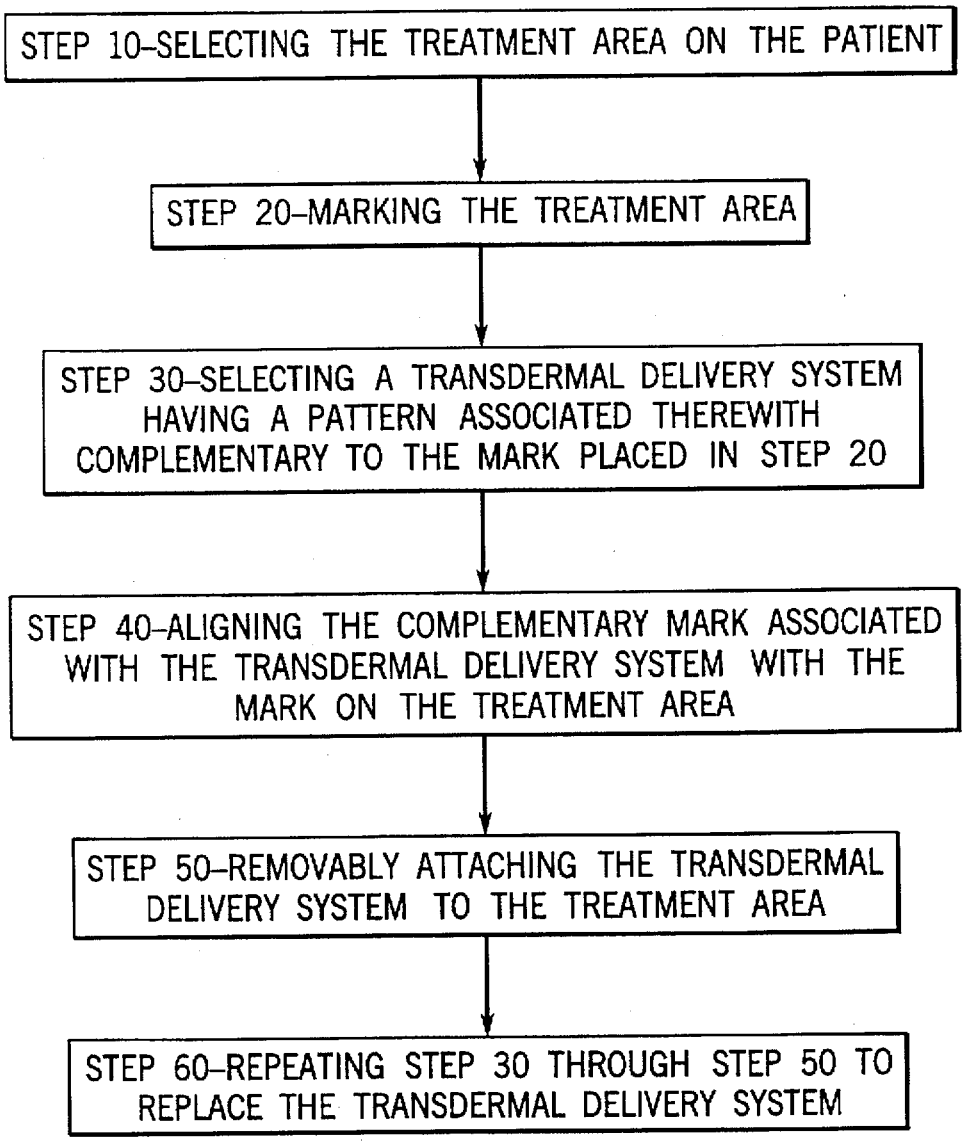
FIG. 3 is a flowchart illustrating the steps of one embodiment of the treatment method of the present invention.

In FIG. 3, a flowchart illustrating the steps of one embodiment of the treatment method of the present invention is provided. According to the method, the appropriate area for treatment by a transdermal delivery system is located in step 70. Next, an marking device (e.g., ink stamp) is selected and used to place a mark in connection with the appropriate treatment area in step 80. In step 90, a transdermal delivery system including a complementary pattern to the mark placed in step 80 is selected. Next, in step 100, the transdermal delivery system is aligned with the mark associated with the treatment area and removably secured into position. In step 110, the transdermal delivery system is removably attached to the treatment area. Finally, in step 120, steps 90 and 110 are repeated as required by the appropriate treatment regimen for treatment of the affected area.

Using the method and kit of the present invention, a patient can accurately and consistently self-administer prolonged treatment of an illness or infection without the assistance of medical personnel. Even where a medical professional assists the patient in the initial location of the appropriate treatment area (step 70), the patient can thereafter complete the treatment regiment, often spanning many months or even years, without the substantial involvement of the heath professional, thereby significantly reducing the cost and time burden associated with such treatments.

Although preferred embodiments of the invention have been illustrated in the accompanying drawings and described in the foregoing Detailed Description, it will be understood that the invention is not limited to the embodiments disclosed, but is capable of numerous rearrangements and modifications of parts and elements without departing from the spirit of the invention.

I claim:

1. A kit for assisting with the positioning and placement of a transdermal delivery system, comprising:

means for placing a mark on an area of a patient in need of treatment; and at least one transdermal delivery system having associated therewith a pattern complementary to the mark made by the means for placing a mark;

said transdermal delivery system capable of being positioned and placed on the treatment area by aligning the pattern associated with the transdermal delivery system with the mark made by the means for placing a mark.

2. The kit of claim 1, wherein the means for placing a mark is an ink stamp.

3. The kit of claim 2, wherein the ink stamp uses indelible ink.

4. The kit of claim 1, wherein the means for placing a mark includes the use of an indelible ink.

5. The kit of claim 1, wherein the mark placed by the means for making a mark comprises a horizontal line and a vertical line connected at their proximal endpoints and forming an "L" shape.

6. The kit of claim 1, wherein the mark placed by the means for making a mark comprises a horizontal line and a vertical line connected at their proximal endpoints and forming any fixed divergent angle.

7. The kit of claim 1, wherein the mark placed by the means for making a mark comprises a horizontal line and a vertical line connected at their midpoints and forming a "+" shape.

8. The kit of claim 1, wherein the mark placed by the means for making a mark comprises a single line or shape capable of alignment with a complementary line or shape.

9. The kit of claim 1, wherein the mark placed by the means for making a mark comprises a plurality of lines or shapes capable of alignment with a complementary plurality of lines or shapes.

10. The kit of claim 1, wherein the transdermal delivery system comprises a patch.

11. The kit of claim 10, wherein the patch is multi-layered, at least one of said layers being transparent or translucent.

12. The kit of claim 1, wherein the complementary pattern associated with the transdermal delivery system is located on the underneath surface of the transdermal delivery system.

13. The kit of claim 11, wherein the patch is aligned with the mark placed by the means for placing a mark by viewing the mark associated with the treatment area through the patch.

14. A method for positioning and placing a transdermal delivery system, comprising the steps of:

(1) selecting an area of a patient in need of treatment;

(2) marking the area with a mark;

(3) selecting a transdermal delivery system having a pattern associated therewith complementary to the mark;

(4) aligning the complementary pattern of the transdermal delivery system with the mark on the treatment area; and (5) removably attaching the transdermal delivery system to the treatment area.

15. The method of claim 14, wherein the mark is made with an ink stamp.

16. The method of claim 15, wherein the ink stamp uses indelible ink.

17. The method of claim 14, wherein the transdermal delivery system is a patch.

18. The method of claim 14, wherein the transdermal delivery system is a multi-layered patch, at least one of said layers being transparent or translucent.

19. The method of claim 14, further including the step of repeating the steps of (3) selecting a transdermal delivery system, (4) aligning the complementary pattern, and (4) removably attaching as needed at such time the transdermal delivery system is replaced.

20. A method for positioning and placing a transdermal delivery system, comprising the steps of:

(1) selecting an area of a patient in need of treatment;

(2) marking the area with an indelible ink mark;

(3) selecting a transdermal delivery system having a pattern associated therewith complementary to the mark;

(4) aligning the complementary pattern of the transdermal delivery system with the mark on the treatment area;

(5) removably attaching the transdermal delivery system to the treatment area; and (6) repeating steps (3)–(5) above to replace the transdermal delivery system.

* * * * *